United States Patent [19]

Winston et al.

[11] Patent Number: 4,663,153
[45] Date of Patent: May 5, 1987

[54] SODIUM BICARBONATE-CONTAINING TOOTH POWDER

[75] Inventors: Anthony Winston, East Brunswick; Anthony Ansaldi, Mt. Arlington; Norman Usen, Marlboro, all of N.J.

[73] Assignee: Church & Dwight Co., Inc., Piscataway, N.J.

[21] Appl. No.: 763,537

[22] Filed: Aug. 8, 1985

Related U.S. Application Data

[60] Division of Ser. No. 628,855, Jul. 9, 1984, Pat. No. 4,547,362, which is a continuation-in-part of Ser. No. 475,355, Mar. 14, 1983, abandoned.

[51] Int. Cl.$^4$ .......................... A61K 7/16; A61K 7/18
[52] U.S. Cl. .......................................... 424/52; 424/49
[58] Field of Search ...................................... 424/49-58

[56] References Cited

U.S. PATENT DOCUMENTS

| | | | |
|---|---|---|---|
| 1,082,681 | 12/1913 | Danner | 424/49 |
| 1,112,180 | 9/1914 | Westenfelter | 167/93 |
| 1,297,494 | 3/1919 | Rhein | 424/55 |
| 1,716,035 | 2/1927 | Donchi | 424/55 |
| 1,943,467 | 2/1932 | Biey | 424/50 |
| 2,024,146 | 12/1935 | Crowther | 424/49 |
| 2,035,267 | 3/1936 | Fleischmann | 424/53 |
| 2,128,917 | 9/1938 | Crocker | 167/93 |
| 2,196,150 | 4/1940 | Heald et al. | 424/57 |
| 2,196,194 | 4/1940 | Schulerud | 424/49 |
| 2,216,816 | 10/1940 | Kuever | 424/57 |
| 2,519,665 | 8/1950 | Klippert | 424/57 |
| 2,550,207 | 4/1951 | Tainter et al. | 424/49 |
| 2,723,217 | 11/1955 | Gershon et al. | 424/57 |
| 2,820,000 | 1/1958 | Menzies | 424/49 |
| 2,941,926 | 6/1960 | Sallmann et al. | 424/57 |
| 3,003,919 | 10/1961 | Broge | 424/49 |
| 3,060,098 | 10/1962 | Gershon | 424/57 |
| 3,325,368 | 6/1967 | Wood | 424/57 |
| 3,330,732 | 7/1967 | Muhler | 424/49 |
| 3,450,813 | 6/1969 | Muhler | 424/49 |
| 3,647,381 | 3/1972 | Relter | 424/49 |
| 3,935,304 | 1/1976 | Januszewski et al. | 424/49 |
| 3,935,305 | 1/1976 | Delaney et al. | 424/49 |
| 3,937,321 | 2/1976 | Delaney et al. | 424/49 |
| 3,937,803 | 2/1976 | Delaney et al. | 424/49 |
| 3,937,804 | 2/1976 | Delaney et al. | 424/52 |
| 3,947,570 | 3/1976 | Pensak et al. | 424/49 |
| 3,957,968 | 5/1976 | Cordon | 424/57 |
| 3,989,813 | 11/1976 | Januszewski et al. | 424/54 |
| 4,060,599 | 11/1977 | Cordon | 424/49 |
| 4,089,943 | 5/1978 | Roberts et al. | 424/49 |
| 4,102,992 | 7/1978 | Davis | 424/49 |
| 4,132,770 | 1/1979 | Barth | 424/49 |
| 4,144,322 | 3/1979 | Cordon et al. | 424/49 |
| 4,160,227 | 7/1979 | Delaney et al. | 424/49 |
| 4,168,301 | 9/1979 | Pugh et al. | 424/49 |
| 4,276,287 | 6/1981 | Cabardo | 424/49 |
| 4,344,931 | 8/1982 | Aguilar | 424/49 |
| 4,547,362 | 10/1985 | Winston et al. | 424/49 |

FOREIGN PATENT DOCUMENTS

1413641 11/1975 United Kingdom.
1413642 11/1975 United Kingdom.
1413643 11/1975 United Kingdom.
2112642A 7/1983 United Kingdom.

OTHER PUBLICATIONS

Lehne et al., Clinical Preventive Dentistry 5(1):17-18, Jan.-Feb. 1983, Abrasivity of Sodium Bicarbonate

*Primary Examiner*—Shep K. Rose
*Attorney, Agent, or Firm*—Stiefel, Gross, Kurland & Pavane

[57] ABSTRACT

A tooth powder comprising at least about 50% by weight of sodium bicarbonate particles, wherein said sodium bicarbonate particles have a median particle size in the range of about 74 to 210 microns, flavoring and sweeteners. Fluoridating agents and second abrasives may also be included in the tooth powder.

10 Claims, No Drawings

SODIUM BICARBONATE-CONTAINING TOOTH POWDER

This is a division of application Ser. No. 628,855 filed July 9, 1984, now U.S. Pat. No. 4,547,362; which application was a continuation in-part of application Ser. No. 475,355 filed Mar. 14, 1983, now abandoned.

BACKGROUND OF THE INVENTION

This invention relates to a sodium bicarbonate-containing tooth powder. More particularly, this invention relates to a tooth powder containing sodium bicarbonate particles of particular sizes, which powder has been found to exhibit improved flavor, flow and abrasivity characteristics as compared with prior tooth powders containing commercial baking powder.

Many different dentifrice compositions are known for cleaning, whitening, and preserving the teeth. Many of these dentifrice compositions include a high content of water-insoluble abrasives, such as dicalcium phosphate, which aid in preventing pellicle and stain build-up on the teeth. In order to preserve the teeth as much as possible, it is widely accepted that the least abrasive material necessary to remove plaque and stain should be used in dentrifice compositions.

Most dentifrices formulated today are in the form of a paste, gel or powder. Toothpastes and gels generally contain, in addition to the abrasive material, humectants, water, thickeners, surfactants, flavors and sweeteners. Tooth powders generally contain only abrasives, flavor, sweetener and sometimes a surfactant. Both types of products sometimes contain additional ingredients for special functional or aesthetic reasons, for example, fluoridating or coloring agents.

Toothpastes and gels have gained wider consumer acceptance than powders since they tend to be more convenient to use. However, powder formulations have certain advantages over toothpastes. For example, humectants, thickeners and water serve no useful purpose in the actual cleaning of teeth but are needed to provide stability to the desired paste or gel form. Powders do not require these ingredients.

One drawback of pastes and gels is the cost of the non-cleaning ingredients. Pastes and gels usually contain 20-50% humectant and thickener, representing a disproportionate share (30%-50%) of the cost of the finished toothpaste or gel. Tooth powders, which may contain up to 99% useful abrasive materials, eliminate the need for the costly (non-cleaning) humectant and thickener ingredients.

A further drawback of pastes and gels is the difficulty of ensuring that these products have the right consistency, are stable and that the ingredients are compatible. Tooth powders, in contrast, are much easier to formulate.

Baking soda particles are relatively soft as compared to most conventional abrasive materials used in dentifrice compositions. The American Dental Association has recommended that "if only a slight degree of abrasion is necessary to keep from staining, baking soda will usually be found satisfactory." *Accepted Dental Therapeutics,* pp. 340–341 (38th Ed., 1979). Toothpaste formulations containing sodium bicarbonate particles as a cleansing agent for teeth have been previously disclosed. See, for example, U.S. Pat. No. 3,943,240 (Delaney et al) and similar patents which disclose a toothpaste composition containing at least about 20%, preferably at least about 30% sodium bicarbonate particles. The size of the sodium bicarbonate particles in the disclosed toothpaste compositions may vary; but it is preferred that a major portion of the particles be above 0.01 mm and below 0.4 mm in diameter. U.S. Pat. No. 2,128,917 (Crocker) also discloses a sodium bicarbonate-containing toothpaste. Crocker discloses that the sodium bicarbonate comprises close to 50% by weight of the toothpaste and that the sodium-bicarbonate particles may be sifted through a #200 mesh sieve (74 microns).

Formulation stability is a frequent problem with sodium bicarbonate-containing pastes or gels. Sodium bicarbonate is unstable in an aqueous solution and releases carbon dioxide gas. See, e.g., U.S. Pat. No. 3,943,240 at column 1, lines 32–34. Also, sodium bicarbonate is not always compatible with other abrasive materials in pastes and gels. See, e.g., U.S. Pat. No. 3,943,240 at column 2, lines 58–62. In contrast, sodium bicarbonate is stable as a dry powder and is compatible in almost any proportion with most other dry ingredients. Thus, sodium bicarbonate-containing tooth powders have decided advantages over sodium bicarbonate-containing toothpastes or gels.

In addition to the above advantages of a sodium bicarbonate-containing tooth powder, it is possible to formulate a tooth powder having a much higher proportion of sodium bicarbonate than is possible in toothpastes or gels. Sodium bicarbonate gives a clean, fresh feeling to the mouth. Sodium bicarbonate also helps to deodorize the oral cavity by neutralizing acidic odors. Thus, it is desirable to maximize the sodium bicarbonate content of a dentifrice. However, because of stability problems, it is difficult, if not impossible, to provide more than about 60% sodium bicarbonate in a paste or gel and maintain the product in usable form. A tooth powder, however, may contain higher levels of sodium bicarbonate.

Thus, it is desirable to provide a dentifrice in the form of a tooth powder in which a major proportion of the ingredients comprises sodium bicarbonate particles.

Several tooth powders containing sodium bicarbonate particles have been previously described.

U.S. Pat. No. 1,082,681 (Danner), for example, discloses a tooth powder containing agglomerated sodium bicarbonate granules having a fineness of about #30 mesh sieve (595 microns) which break down into powdered form in the mouth. The granular particles are produced by moistening with water, sieving and drying. Such a product has an excessively granular feel in the mouth. Moreover, as a result of the pre-moistening and drying some decomposition of the bicarbonate occurs, the resulting material having a slightly bitter taste.

U.S. Pat. No. 2,024,146 (Crowther) discloses a tooth powder containing about 15% by weight of sodium bicarbonate, about 30% and two other more abrasive materials (magnesium oxide and calcium carbonate), and at least 12 other ingredients. The tooth powder passes through a #40 mesh sieve (420 microns).

U.S. Pat. No. 4,276,287 (Cabardo, Jr.) discloses a periodontal powder containing about ⅔ potassium alum and ⅓ sodium bicarbonate, together with small quantities of antiseptics, flavoring agents, sweenteners and colorants. The particle size range of the sodium bicarbonate powder constituent is not specified in the patent. Moreover, because of the strongly acidic, astringent flavor of the alum, the degree of granulation of the minor quantity of the sodium bicarbonate present in the tooth powder would have not effect on the taste or mouth feel of this product.

The multipurpose baking soda of commerce is also recommended for use as a tooth powder; such material consists essentially of sodium bicarbonate particles having a median particle size in the range of 44–73 microns.

One major problem encountered in the formulation of a tooth powder having a major proportion by weight of abrasive particles, including sodium bicarbonate particles, is reducing the abrasiveness of the tooth powder to acceptable levels. Excessive abrasiveness can lead to loss of tooth enamel and erosion of exposed dentin. Abrasiveness is of particular concern in tooth powders since the concentration of abrasives is much higher than in pastes or gels. Also, the ingredients present in the pastes and gels often serve to moderate the abrasivity of the overall formulation.

Another major problem encountered in formulating a tooth powder containing sodium bicarbonate particles is the salty taste of sodium bicarbonate. It has now been found that the salty flavor decreases and can be more readily masked if coarser grades of sodium bicarbonate are used in the tooth powder. In order to prepare a sodium bicarbonate-containing dentifrice which is not too salty, the use of large sodium bicarbonate particles is indicated. However, it is known that abrasivity generally increases with increasing particle size. See, for example, *Cosmetic Science and Technology*, Vol. 1, pages 427, 428 (Wiley-Interscience, 2d Ed., 1972); Tainter, M. L., and S. Epstein, 30 *J. Am. Dent. Assoc.*, pp. 1036–1045 (1943); M. L. Smith, *J. Soc. Chem. Ind.*, pp. 691–697 (Aug. 23, 1935). Thus, with the higher levels of sodium bicarbonate pesent as the principal abrasive in a tooth powder, one would except that a significant increase in the mean particle size would increase the abrasivity.

In accordance with the present invention, a sodium bicarbonate-containing tooth powder is provided which is effective in preventing pellicle and stain build-up on the teeth, but is not so abrasive as to deleteriously affect tooth enamel, cementum, or dentin. Moreover, and notwithstanding prior expectations, the sodium bicarbonate particles are sufficiently coarse so that the tooth powder is not excessively salty but leaves the user with a fresh mouth taste.

SUMMARY AND DETAILED DESCRIPTION OF THE INVENTION

In accordance with the present invention a tooth powder is provided comprising at least 50% by weight of sodium bicarbonate particles, wherein the sodium bicarbonate particles have a median particle size within the range of about 74 to 210 microns. Preferably, the median size of the sodium bicarbonate particles in the tooth powder is within the range of about 74 to 149 microns. It has surprisingly been found that such a tooth powder is lower in abrasivity than tooth powders in which the median particle size of sodium bicarbonate is less than 74 microns. In addition, the sodium bicarbonate particles in a tooth powder according to the present invention are sufficiently coarse so that the tooth powder is not unduly salty.

Commercially available, "multipurpose" baking soda, referred to by Lehne et al in "Abrasivity of Sodium Bicarbonate", 5 *Clincial Preventive Dentistry*, p. 17 (1983), has a median particle size of between 44 and 73 microns, typically about 64 microns. The formulation of the present invention by comparison, contains sodium bicarbonate having a mean particle size of at least 74 microns, and preferably about 96 microns. The variation in particle size between the commercially available sodium bicarbonate and this more granular sodium bicarbonate has been found quite significant in the tooth powder compositions of the invention. The more granular sodium bicarbonate particles result in an improved dentifrice which is less salty, has better flow characteristics, has less tendency to cake and suprisingly provides lower abrasivity, despite its larger particle size, than commercially available multipurpose baking soda.

The tooth powder of the present invention comprises at least about 50% by weight of the sodium bicarbonate within the specified particle size range. Preferably, the tooth powder comprises about 75% to 98% by weight of sodium bicarbonate. Most preferably, the tooth powder comprises about 90% to 98% by weight of sodium bicarbonate.

Desirably, the tooth powder also includes at least a suitable flavoring agent and sweetener. Examples of suitable flavoring agents include the flavoring oils, for example, oils of spearmint, peppermint, wintergreen, sassafras, clove, sage, eucalyptus, marjoram, cinnamon, lemon and orange, as well as sodium methylsalicylate. The flavoring agent may be present in the tooth powder in an amount up to about 3% by weight of the tooth powder, preferably, in an amount within the range of from about 0.05% to 3%. Most preferably, the flavoring agent is present in an amount of about 2% by weight of the tooth powder. A carrier for the flavoring agent may optionally also be present in the tooth powder. Such carriers are well known to those skilled in the art. Suitably, the carrier is present in an amount of up to about 5% by weight of the tooth powder.

A sweetening agent is also included in the tooth powder of the present invention. Suitable sweeteners include lactose, maltose, sorbitol, aspartame, and saccharin. The amount of sweetener present in the tooth powder is within the range of up to about 3% by weight of the tooth powder, preferably, in an amount within the range of from about 0.20% to 3.0%. The flavoring and sweetening agents help to mask the salty taste of the sodium bicarbonate.

The tooth powders of the present invention may contain other ingredients in addition to the sodium bicarbonate, flavoring agent and sweetener. The tooth powder may thus contain up to about 50% by weight of an additional abrasive material. It is desirable that the additional abrasive be low in abrasivity, preferably with an RDA (radioactive dentin abrasion) value in the range of about 20 to 100. Abrasive materials suitable as additional abrasives in the tooth powders hereof are well known in the art and include, calcium carbonate, e.g., chalk, dicalcium phosphate, silica, alumina, titanium dioxide, zirconium silicate, and the like, or mixtures thereof. The optimum particle sizes to be used for the additional abrasive vary with the particular material, as abrasivity is a function of particle size and the hardness and shape of the particles used. Typically the particle size of the additional abrasive would be in the range of about 0.01 to 25 microns. Abrasives so useful are described in *Cosmetics, Science And Technology*, 2nd Ed., Vol. I, Chapter XIV, "Dentrifrices", pp. 461–484, Wiley-Interscience. Examples include various grades of calcium carbonates having median particle sizes of less than 3 microns (John and E. Sturge, Ltd.), or between 2 and 7 microns (Chas. Pfizer and Co., Inc.). Dicalcium phosphate dihydrate which is so suitable is described as having a median particle size within the range of 15 to 20 microns (Monsanto Chemical Co.).

Also useful is silica gel (hydrated silica), which is described as having a particle size in the range of about 8 to 13 microns. Microcrystalline aluminum hydroxide, having particle sizes between 0.025 and 0.5 microns (U.S. Pat. No. 2,550,207) and titanium dioxide in the range of about 0.05 to 0.8 microns (U.S. Pat. No. 3,937,803) may similarly be utilized. Other materials suitable for use as additional abrasives in the tooth powder of this invention are disclosed in U.S. Pat. No. 3,937,803 and include chalk having a particle size of 20 microns, preferably 1–10 microns, silica of particle size 2 to 10 microns, alumina of particle size 2 to 10 microns, and zirconium silicate of particle size 0.3 to 3 microns.

A significant advantage of the present tooth powder formulation over sodium bicarbonate based toothpastes is the ability to combine the sodium bicarbonate with dicalcium phosphate dihydrate as an additional abrasive. Use of the latter material in a dentifrice is desirable because it is a soft abrasive (2.5 on Mohs hardness scale; see Cosmetic Science, Vol. I, M. M. Breuer, p. 49, 1978, Academic Press). In a paste formulation, sodium bicarbonate and dicalcium phosphate dihydrate are incompatible; even on short term storage mixtures of these abrasive produce considerable quantities of gas (for example, see U.S. Pat. No. 3,937,321). The interaction between sodium bicarbonate and dicalcium phosphate dihydrate is not, however, possible in the dry tooth powder of the present invention.

An anti-caking agent, such as silica or tricalcium phosphate, may also be included in the present tooth powder. Suitably, the amount of anti-caking agent is within the range of up to about 2% by weight of the tooth powder.

An organic surface active agent may also be incorporated in the tooth powder. The surface active agent aids in cleaning the teeth and also improves the foaming properties of the tooth powder. Suitable surface active agents are well known in the art and include, for example, water-soluble salts of the higher alkyl sulfates, such as sodium lauryl sulfate; water-soluble salts of sulfonated monoglycerides of fatty acids, such as sodium coconut monoglyceride sulfonate; salts of amides of higher fatty acids with lower aliphatic amino acids, such as sodium lauryl sarcosinate, and the like. The surface active agent may be present in the tooth powder in amounts ranging up to about 2% by weight.

The tooth powder of the present invention may additionally contain a fluoridating agent to aid in preventing dental caries. Many fluoridating agents suitable for use in a dentifrice composition are known. Among these are sodium, potassium, ammonium, lithium, and amine fluorides, monofluorophosphate salts such as sodium, potassium, ammonium, and lithium monofluorophosphate, and other fluoridating agents well known to those skilled in the art. The fluoridating agents are present in an effective but non-toxic amount, e.g., in amounts of up to about 2% by weight of the tooth powder. Preferably, the tooth powder of the present invention will contain about up to 0.5% by weight of sodium fluoride or up to about 1% by weight of sodium monofluorophosphate as the fluoridating agent.

In a preferred form, the tooth powder of the present invention contains about 75% to 98%, most preferably about 90% to 98% by weight of sodium bicarbonate particles having a median particle size within the range of about 74 to 149 microns, about 0.5–3% by weight of a flavoring agent, about 0.2–3% by weight of a sweetener, and about 0.22% by weight of sodium fluoride.

The following examples illustrate the practices of the present invention and sample formulations thereof. In the examples all parts and percentages are given by weight.

EXAMPLES 1-3

Tests were run to show the effect of the concentrations and particle sizes of sodium bicarbonate particles on the abrasive characteristics of dentifrice compositions. In the first three pairs of experiments a preferred tooth powder formulated in accordance with the invention and consisting essentially of sodium bicarbonate having a median particle size within the range of from 74 to 149 microns[1] was compared, in various concentrations in water, with a multipurpose baking soda having a median particle size of 44-73 microns. The various bicarbonate materials were mixed with 50 ml of water containing 0.5% of carboxymethyl cellulose (CMC) as a thickener. The mixtures were then subjected to the well-known radioactive dentin abrasion (RDA) and radioactive enamel abrasion (REA) tests. The results are shown in Table I below. Table I also shows the results when comparable RDA and REA tests were performed on two commmercial toothpastes which do not contain sodium bicarbonate. Control D was "Crest" toothpaste containing stannous fluoride and a hydrated silica abrasive. Control E was "Colgate" dental cream containing dicalcium phosphate as the abrasive:

[1] The tooth powder incorporated 97.32% of the sodium bicarbonate, 0.8% of a peppermint flavoring agent (as a spray dried powder containing 20% of the flavor oil), 1.2% of a saccharin sweetener, and 0.22% sodium fluoride.

TABLE I

COMPARATIVE ABRASIVE CHARACTERISTICS OF SODIUM BICARBONATE OF VARYING PARTICLE SIZES

| Example or Control | Material | Concentration | Approximate % $NaHCO_3$ | RDA | REA |
|---|---|---|---|---|---|
| Ex. 1 | $NaHCO_3$ (74–149 microns) | 10 g $NaHCO_3$ in 50 ml $H_2O$ | 16.67% | 21 | 16 |
| Control A | $NaHCO_3$ (44–73 microns) | 10 g $NaHCO_3$ in 50 ml $H_2O$ | 16.67% | 25 | 16 |
| Ex. 2 | $NaHCO_3$ (74–149 microns) | 25 g $NaHCO_3$ in 50 ml $H_2O$ | 33.34% | 52 | 16 |
| Control B | $NaHCO_3$ (44–73 microns) | 25 g $NaHCO_3$ in 50 ml $H_2O$ | 33.34% | 62 | 16 |
| Ex. 3 | $NaHCO_3$ (74–149 | 50 g $NaHCO_3$ in 50 ml $H_2O$ | 50.00% | 54 | 13 |

TABLE I-continued

COMPARATIVE ABRASIVE CHARACTERISTICS OF
SODIUM BICARBONATE OF VARYING PARTICLE SIZES

| Example or Control | Material | Concentration | Approximate % NaHCO$_3$ | RDA | REA |
|---|---|---|---|---|---|
| Control C | NaHCO$_3$ (44–73 microns) | 50 g NaHCO$_3$ in 50 ml H$_2$O | 50.00% | 68 | 20 |
| Control D | "Crest" (hydrated silica abrasive) | 25 g/50 ml H$_2$O | — | 67 | 50 |
| Control E | "Colgate" dental cream (dicalcium phosphate abrasive) | 25 g/50 ml H$_2$O | — | 46 | 14 |

The data tabulated above demonstrate that sodium bicarbonate particles having a median particle size within the range of 74–149 microns are less abrasive than sodium bicarbonate particles having a median particle size within the range of 44–74 microns.

EXAMPLES 4–5

The abrasivity of sodium bicarbonate particles of different sizes was compared with the abrasive characteristics of the standard abrasive calcium pyrophosphate particles as determined by the RDA test. The results are shown in Table II:

TABLE II

COMPARISON OF ABRASIVE CHARACTERISTICS
OF SODIUM BICARBONATE OF VARYING PARTICLE
SIZES WITH CALCIUM PYROPHOSPHATE

|  | Median Particle Size | Average RDA |
|---|---|---|
| Calcium pyrophosphate |  | 100 |
| Baking soda | 44 microns | 39 |
| Baking soda | 44–73 microns | 28 |
| Baking soda | 74 microns | 25 |
| Baking soda | 149 microns | 22 |

The results show that sodium bicarbonate is much lower in abrasivity than calcium pyrophosphate. The results also show that the abrasivity of sodium bicarbonate particles decreases as the median particle size increases. Thus, a tooth powder low in abrasivity and low in salty flavor can be formulated which is comprised of a major proportion by weight of sodium bicarbonate particles having a median size within the specified range.

EXAMPLE 6

The saltiness and taste of two bicarbonate materials of varying particle sizes were compared by a 14 member taste panel. The results are summarized in Table III below:

TABLE III

COMPARISON OF SALTINESS AND
TASTE OF BICARBONATES HAVING SIZES OF 44–73
MICRONS AND 149–210 MICRONS

| Subjective Opinion | Example 6 (149–210 microns) | Control I (44–73 microns) |
|---|---|---|
| More Salty | 1 | 13 |
| Taste Preferred | 9 | 5 |

The panel views respecting the relative saltiness were significant at the 95% confidence level.

EXAMPLES 7–8

Comparisons of flowability of the various grades of sodium bicarbonate show the more granular grades to flow more freely, an important advantage in terms of product dispensability. In addition, lumping studies show the more granular grades to lump less on storage. The results of the flow and agglomeration studies are summarized in Table IV below:

TABLE IV

COMPARISON OF FLOW AND AGGLOMERATION
CHARACTERISTICS OF BICARBONATES OF
VARYING PARTICLE SIZES

| Example or Control | Median Particle Range | Flow Rating* | % Total Lumps After 7 Days (90/80)** | % Hard Lumps After 7 Days (90/80) |
|---|---|---|---|---|
| Ex. 7 | 149–210 microns | 1 | — | — |
| Ex. 8 | 74–149 microns | 5 | 28 | 0 |
| Control J | 44–73 microns | 11 | 68 | 24 |
| Control K | Less than 44 microns | 14 | 92 | 52 |

*Allied Flow tester; the lower the number the better the flow.
**Tests were performed at 90° C. with an 80% relative humidity.

EXAMPLE 9

With regard to flavor preferences, panel tests on sodium bicarbonate based powdered formulations containing 98.08% sodium bicarbonate, 0.2% peppermint oil (supplied as spray dried powder added at 1% level and containing 20% flavor oil), 0.8% saccharin and 0.12% sodium fluoride showed that the saltiness decreases and taste preference increases as the particle size of the sodium bicarbonate used increases. The results are summarized in Table V below:

TABLE V

COMPARISON OF TASTE AND SALTINESS OF
BICARBONATES HAVING VARYING PARTICLE SIZES
OF PANELISTS SELECTING:

| Subjective Opinion | Example 9 (74 microns) | vs. | Control L (44–73 microns) |
|---|---|---|---|
| Prefer Taste | 14[1] |  | 6[1] |
| More Salty | 6[2] |  | 13[2] |
| Major Positive* | Taste (11)[1] |  | Taste (3)[1] |

|  | Control L (44–73 microns) | vs. | Control M (Less than 44 microns) |
|---|---|---|---|
| Prefer Taste | 13[1] |  | 4[1] |
| More Salty | 5 |  | 10 |

TABLE V-continued
COMPARISON OF TASTE AND SALTINESS OF BICARBONATES HAVING VARYING PARTICLE SIZES
# OF PANELISTS SELECTING:

| Major Positive* | Taste (10)[1] | Taste (2)[1] |
|---|---|---|

[1]Significant at the 90-95% confidence level.
[2]Significant at the 85-90% confidence level.
*Major positive refers to the characteristic preferred most by the panelists.

Further Examples Of Sodium Bicarbonate Tooth Powder Formulations of the Invention

| | % |
|---|---|
| Example 10 | |
| Sodium bicarbonate (median particle size 74 to 149 microns) | 96.18 |
| Sodium fluoride | 0.22 |
| Magnesium oxide | 0.10 |
| Saccharin | 1.50 |
| Peppermint flavor* | 2.00 |
| | 100.00 |
| Example 11 | |
| Sodium bicarbonate (median particle size 74 to 149 microns) | 86.00 |
| Dicalcium phosphate dihydrate (median particle size 15-20 microns) | 10.00 |
| Sodium monofluorophosphate | 0.76 |
| Magnesium oxide | 0.10 |
| Saccharin | 1.34 |
| Spray dried flavor (containing 20% oil) | 1.80 |
| | 100.00 |
| Example 12 | |
| Sodium bicarbonate (median particle size 74-149 microns) | 91.18 |
| Hydrated silica (median particle size 8-13 microns) | 5.0 |
| Sodium fluoride | 0.22 |
| Magnesium oxide | 0.10 |
| Saccharin | 1.50 |
| Spray dried flavor (containing 20% oil) | 2.00 |
| | 100.00 |
| Example 13 | |
| Sodium bicarbonate (median particle size 74-149 microns) | 56.4 |
| Dicalcium phosphate dihydrate (median particle size 15-20 microns) | 40.00 |
| Sodium lauryl sulfate | 1.5 |
| Saccharin | 0.9 |
| Spray dried flavor (containing 20% oil) | 1.2 |
| | 100.00 |

*The flavor is provided as a spray dried powder containing 20% flavor oil.

While dentifrice compositions and the method of cleaning teeth of the invention have been described by reference to specific embodiments, this was for purposes of illustration only and should not be construed to limit the spirit or scope of the invention.

We claim:

1. A dentifrice composition comprising at least 50% by weight of sodium bicarbonate particles as a dental abrasive material, said sodium bicarbonate particles having a median particle size within the range of 74 to 210 microns; and from 0.1 to 2% by weight of a fluoridating agent, said dentifrice composition being in the form of a tooth powder.

2. The dentifrice composition of claim 1, further containing from 0.05% to 3.0% by weight of a flavoring agent, and 0.20 to 3.0% by weight of a sweetener.

3. The dentifrice composition of claim 1, wherein the median particle size of said sodium bicarbonate particles is within the range of 74 to 149 microns.

4. The dentifrice composition of claim 1, comprising between 75% and 98% by weight of the sodium bicarbonate abrasive.

5. The dentifrice composition of claim 4, wherein the sodium bicarbonate particles have a median particle size within the range of 74 to 149 microns.

6. A method of cleaning the teeth and gums, comprising applying a tooth powder to said teeth and gums, said tooth powder comprising at least about 50% by weight of sodium bicarbonate particles having a median particle size within the range of 74 to 210 microns, and from 0.1 to 2% by weight of a fluoridating agent.

7. The method of claim 6, wherein the tooth powder contains from 0.05 to 3.0% by weight of a flavoring agent, and from 0.20% to 3.0% of a sweetener.

8. The method of claim 6, wherein the median particle size of the sodium bicarbonate particles in the tooth powder is within the range of 74 to 149 microns.

9. The method of claim 6, wherein the sodium bicarbonate particles comprise from 75% to 98% by weight of the tooth powder.

10. The method of claim 6, wherein the sodium bicarbonate particles comprise from 75% to 98% by weight of the tooth powder, and the median particle size of the sodium bicarbonate particles is within the range of 74 to 149 microns.

* * * * *

UNITED STATES PATENT AND TRADEMARK OFFICE
CERTIFICATE OF CORRECTION

PATENT NO. : 4,663,153

DATED : May 5, 1987

INVENTOR(S) : Anthony Winston et al.

It is certified that error appears in the above-identified patent and that said Letters Patent is hereby corrected as shown below:

```
Col. 2, line 56: "and" should read --of--.
Col. 3, line 01: "not" should read --no--.
Col. 3, line 26: the period (.) after "However" should be a
                 comma (,).
Col. 3, line 34: "except" should read --expect--.
Col. 4, line 07: "dentrifice" should read --dentifrice--.
Col. 4, line 63: "Dentrifrice" should read --Dentifrice--.
Col. 4, line 65: "carbonates" should read --carbonate--.

Col. 5, line 20: "dentrifice" should read --dentifrice--.
Col. 6, line 28: "dentrifice" should read --dentifrice--.
```

Signed and Sealed this

Third Day of May, 1988

*Attest:*

DONALD J. QUIGG

*Attesting Officer*  *Commissioner of Patents and Trademarks*